United States Patent [19]

Alvarado

[11] Patent Number: 4,581,027
[45] Date of Patent: Apr. 8, 1986

[54] SANITARY NAPKIN WITH MEANS FOR DISPOSAL

[76] Inventor: Daniel B. Alvarado, Insurgentes Sur 1228, C.P. 03210, Mexico City, Mexico

[21] Appl. No.: 729,615

[22] Filed: May 2, 1985

[51] Int. Cl.$^4$ .............................................. A61F 13/16
[52] U.S. Cl. .................................................. 604/385
[58] Field of Search ................ 604/385, 358, 386, 387

[56] References Cited

U.S. PATENT DOCUMENTS

| | | | |
|---|---|---|---|
| 3,035,578 | 5/1962 | Elmore | 604/385 |
| 3,230,956 | 1/1960 | Kargul | 604/385 |
| 3,274,999 | 9/1966 | Robinson | 604/385 |
| 3,604,423 | 9/1971 | Fraser | 604/385 |

FOREIGN PATENT DOCUMENTS 868299  5/1961  United Kingdom ................ 604/385

*Primary Examiner*—John D. Yasko
*Attorney, Agent, or Firm*—McGlew and Tuttle

[57] ABSTRACT

A sanitary napkin comprising a fluid transmitting wrapper, a fluid absorbent pad housed within said wrapper, a fluid impervious lamina located between the surface of the absorbent pad and the interior of the garment-side of said wrapper, said impervious lamina also spanning the edges of said absorbent pad to avoid permeation of the body fluids, at least one adhesive band extending along the length of the outer surface of the garment-side of said wrapping for attaching said napkin to an undergarment, and a protecting web covering said adhesive band, is provided with an integral disposal bag which comprises a pair of layers of an impervious material arranged between said impervious lamina and the garment-side of said wrapping, said layers also spanning the side edges of said absorbent pad and being formed by a single sheet of said impervious material folded over itself at its side edges and closed at its ends to constitute said bag, the garment-side layer of said bag being slit throughout its length by means of a cut at the mid line of said napkin for forming a pair of openable flaps, the margins of both of said flaps being provided with an outer adhesive band covered by said protecting web, said adhesive bands providing in use garment attaching means as well as bag sealing means when disposing of said napkin upon opening said flaps and turning said bag inside-out to completely wrap the used napkin.

4 Claims, 8 Drawing Figures

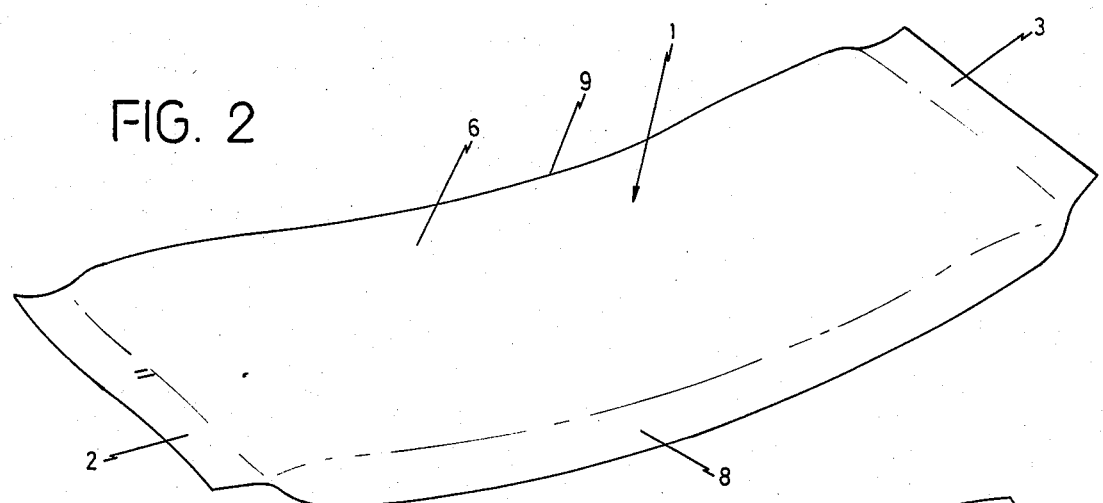
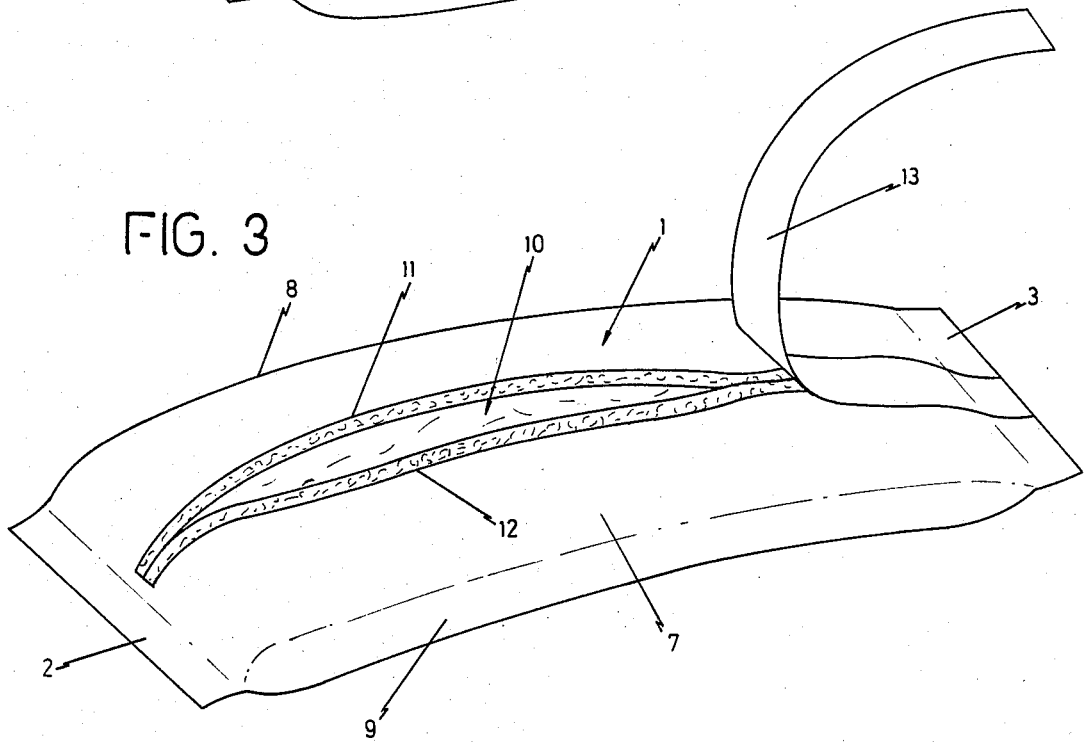

//SANITARY NAPKIN WITH MEANS FOR DISPOSAL

FIELD OF THE INVENTION

The present invention refers to improved sanitary napkins and, more particularly, it is related with a disposal integral means incorporated in a sanitary napkin for facilitating disposal thereof after use.

BACKGROUND OF THE INVENTION

Since the advent of the sanitary napkins, which was a breakthrough in the art of sanitary devices, the problem of disposal of said articles has been one of the most cumbersome features in connection with the use of these devices, because the structure, size and composition of said devices do not lend themselves to an expedite disposal of the same, either by flusing in a toilet or the like, or by disposing thereof through garbage deposits and the like, which has not been regarded as very adequate in view of the unneatness of this type of articles after used. The necessity of wrapping said goods after use in imprevious bags or the like, has created a nuissance for the users and has encouraged some workers to carry out research in connection with the provision of means for disposing of sanitary napkins in the past, without however accomplishing any remarkable success in this field.

For instance, in U.S. Pat. No. 3,604,423 to Fraser, a sanitary napkin is provided with a folded disposable wrapper secured to the outer or garment-side of the pad, said wrapper having the form of a bag having rectangular inner and outer sheets marginally connected by triangular side sheets, one end of said wrapper being releasably connected to the pad whereby, after use of the sanitary napkin, the opposite end portions of the soiled side of the napkin are folded together and the releasable end of the outer sheet of the wrapper is released and pulled around the folded pad to the opposite side, turning the bag inside-out around the pad. An adhesive tape is provided to seal the package for disposal. Although this device solves the problem of disposing of sanitary napkins by wrapping the same in some sort of a bag, the provision of said bag on one of the surfaces of the sanitary napkin, in the form of a completely independent feature of the napkin, produces very serious problems of manufacture, particularly in mass production processes like those used in connection with this type of goods, and on the other hand produces discomfort in the use of the device, as well as certain other disadvantages such as the fact that this bag or wrapper is attached to the napkin in the form of an external patch which renders it impossible to provide the garment side of the napkin with the customary adhesive band to secure said napkin to a garment of the user.

These drawbacks shown by the device of Fraser, and particularly the serious difficulties that may be encountered in connection with mass production processes for attaching the independent and superposed bag to the sanitary napkin, have rendered this device as rather impopular and as not quite acceptable to manufacturers of sanitary napkins up to the present date.

One other solution for the above described problem has been given by Srinivasan et al, U.S. Pat. No. 3,973,567, who provide a sanitary napkin with an adhesive element for attaching to an undergarment of the user, and having a plastic sheet both for protecting the napkin and the adhesive element prior to use and for disposing of the napkin after use. The napkin is provided with a wrapper sheet of flexible material overlying the napkin on its two faces and side edges, which sheet is maintained in its place, prior to use, by the adhesive elements thereof or alternatively by the use of a suitable adhesive band therefor. This same wrapping of the unused napkin serves as a wrapping for disposing of the napkin after use, but the problem with this device is that the wrapping is completely independent and separate from the napkin itself, and merely serves as a wrapping prior to use, which must be completely removed from the napkin in order to enable use thereof, and must be kept appart in the purse of the user or the like, to be thereafter used as a wrapping for the already used sanitary napkin, thus implying the preservation of said wrapping separately from the napkin, which is very frequently a difficult task, particularly for ladies in sport garments who do not carry a purse or the like. The device of Srinivasan et al, therefore, does not solve in any manner the problem of providing an integrated device for disposing of sanitary napkins, and merely substitutes the usual bag or wrapper of the sanitary napkin as sold, by a sheet wrapping which is unfolded to release the napkin for use, and which must be kept separate from the napkin to be thereafter reused in wrapping the used napkin for disposal thereof. Therefore, the device of Srinivasan et al, does not produce any improvement in the means for disposal of sanitary napkins whatsoever.

One other attempt to solve this problem was carried out by Black, U.S. Pat. No. 4,182,336, with a solution which is very similar to that provided by Fraser above, namely, by attaching, to the garment-side surface of the sanitary napkin, a folded receptacle which is thereafter unfolded and used for disposal of the already used sanitary napkin. The only difference between the device of Black and the device of Fraser described above, is that the device of Black is provided attached to the garment-side of the sanitary napkin, over the adhesive band which is used to secure said napkin to an undergarment of the user, which implies that this sack may be provided also for sanitary napkins with adhesive bands for attaching to an undergarment. In accordance with Black, attached to the usual pad type sanitary napkin is a sack-like container or bag made of thin, foldable, moisture-proof material. The bag is attached so that it may be opened to a position to receive the napkin, whereafter the bag with the napkin therein may then be closed for disposal. The device of Black, however, presents the very important drawback that it must be attached over the garment-side face of the sanitary napkin, and covering an important portion of the adhesive band or bands which are used to attach the napkin to the undergarment of the wearer, whereby the efficiency of said adhesive band is considerably diminished, thus producing a drawback which may be regarded as more serious as the problem of disposing of the sanitary napkin after use. On the other hand, the sack or bag of Black, although attached by means of adhesive to one face of the sanitary napkin, is completely external and independent device much like the device of Fraser described above, and also constitutes a condition of discomfort to the wearer, and presents the additional drawback with respect to the device of Fraser, that the bag or sack must be completely teared out from the surface of the sanitary napkin, to thereby produce a completely separate and independent sack-like deposit wherein the sanitary napkin is introduced for disposal. The superposition of this folded sack-like deposit, renders it an independent product of manufacture with respect to the sanitary napkin, whereby this also renders mass production of sanitary napkins containing said sacks very cumbersome and inefficient, and thus the device of Black has also not gained any important proportion of the market in this field.

One other attempt to solve the problem of disposing of sanitary napkins is described and claimed by Baum, U.S. Pat. No. 4,402,689, by providing a sanitary napkin with a baffle approximately twice the width of the conventional baffle, which is normally placed on the garment-side of the face of the sanitary napkin. The baffle is folded over onto itself with the garment facing side having a garment suspension adhesive pattern. After the napkin has been used, the folded portion is unfolded and placed over the top of the napkin where it is adhesively attached by the garment suspension adhesive pattern placed on the garment facing side of the folded portion of the baffle. With this means, the sanitary napkin, after use, is wrapped around the two faces thereof and the two longitudinal edges thereof, but only to form some sort of a roll without any protectin or covering on the longitudinal edges of the napkin, whereby this device is useful only to avoid the user having to touch the soiled napkin surface when disposing of the same. In other words, although the device of Baum may be regarded as suitable for mass production techniques, it is also quite true that said device does not solve the problem of hermetically wrapping the used sanitary napkin for disposal thereof and instead only provides means to dispose of the sanitary napkin by covering the used portion of the same without the user having to touch the soiled napkin surface.

In the U.S. Pat. No. 4,380,450, on the other hand, Reich describes a disposal means for a sanitary napkin, which merely comprises providing a sanitary napkin with an adhesive on at least one end of the same at the body facing side. The adhesive area is provided at a portion of the end extending beyond the absorbent layer and the wrap in this area is folded over to prevent attachment to the body. After the napkin has been used and is ready to be discarded, the wearer opens the folded end and attaches the adhesive surface to the opposite end so that the napkin, when attached, resembles a ring or circle. The used portion of the napkin is at least partially visually screened and there is virtually no compression of the absorbent layer whereby there is no problem of strike-back. The user, on the other hand, does not have to touch the soiled portions of the napkin prior to disposal. The device of Reich, therefore, may not be regarded as a true wrapping for the used napkin for disposal thereof, but rather as a means, similar to the device of Baum, to avoid the necessity for the wearer to touch the soiled surface of the napkin when disposing thereof.

Therefore, all the prior art devices for disposing of used sanitary napkins have left much to desire and the existence of so many types of such devices which may be regarded as inefficient, difficultly manufactured and/or generators or discomfort or inefficiency in the attachment of the napkin to the undergarment of the wearer, proves that for long a device for disposing of a used sanitary napkin has been sought, which may solve the above described problems of disposal, without however, affecting other advantageous characteristics thereof. Up to the present date, however, no worker in the art has been able to produce such a device.

OBJECTS OF THE INVENTION

Having in mind the defects of the prior art disposal means for sanitary napkins, it is an object of the present invention to provide a sanitary napkin with means for disposal, which is of very simple construction, does not modify the general structure of a standard sanitary napkin and is suitable for mass production techniques.

It is one other object of the present invention to provide a sanitary napkin of the above described character which will present all the advantageous characteristics of presently existent sanitary napkins, but which will contain integrated disposal means absolutely inconspicuous and unnoticeable to the wearer.

It is one other and more particular object of the present invention to provide a sanitary napkin of the above described character, which will provide means of disposal suitable for disposing of the sanitary napkins in trash receptacles and the like.

On other and more particular object of the present invention is to provide a sanitary napkin of the above identified character, which will contain means for disposal which will also serve as an impervious barrier on the garment-side of the sanitary napkin to assist in the retention of body fluids within the absorbent pad.

Another object of the present invention is to provide a sanitary napkin of the above described character which will enable the sealing of the means for disposal contained integrally therein, by using the standard adhesive bands provided for attachment to an undergarment.

The foregoing objects and others ancillary thereto are preferably accomplished as follows:

According to a preferred embodiment of the present invention, a sanitary napkin is provided which comprises a fluid transmitting wrapper, a fluid absorbent pad housed within said wrapper, a fluid impervious lamina located between the surface of the absorbent pad and the interior of the garment-side of said wrapper, said impervious lamina also spanning the edges of said absorbent pad to avoid permeation of the body fluids, at least one adhesive band extending along the length of the outer surface of the garment-side of said wrapping for attaching said wrapping to an undergarment, and a protecting web covering said adhesive band, said sanitary napkin comprising an integral disposal bag which in turn comprises a pair of layers of an impervious sheet material arranged between said impervious lamina and the garment-side of said wrapping, said layers also spanning the side edges of said absorbent pad and being formed by a single sheet of said impervious material folded over itself at its side edges and closed at its ends to constitute a bag, the garment-side layer of said bag being slit throughout its lenght by means of a cut at the mid line of said napkin for forming a pair of openable flaps, the margins of both of said flaps being provided with an outer adhesive band covered by said protecting web, said adhesive bands providing in use garment attaching means as well as bag sealing means when disposing of said napkin upon opening said flaps and turning said bag inside-out to completely wrap the used napkin.

BRIEF DESCRIPTION OF THE DRAWINGS

The novel features that are considered characteristic of the present invention are set forth with particularity in the appended claims. The invention itself, however, both as to its organization and its method of operation, together with additional objects and advantages thereof, will best be understood from the following description of a specific embodiment, when read in connection with the accompanying drawings, in which:

FIG. 2 is a perspective view of the sanitary napkin shown in FIG. 1, but showing the body-side of the napkin;

FIG. 3 is a view similar to FIG. 2 but showing the garment-side face of the sanitary napkin, with the disposal means partially open and the protective band partially teared out in order to show inner details thereof;

DETAILED DESCRIPTION

Figure 1:
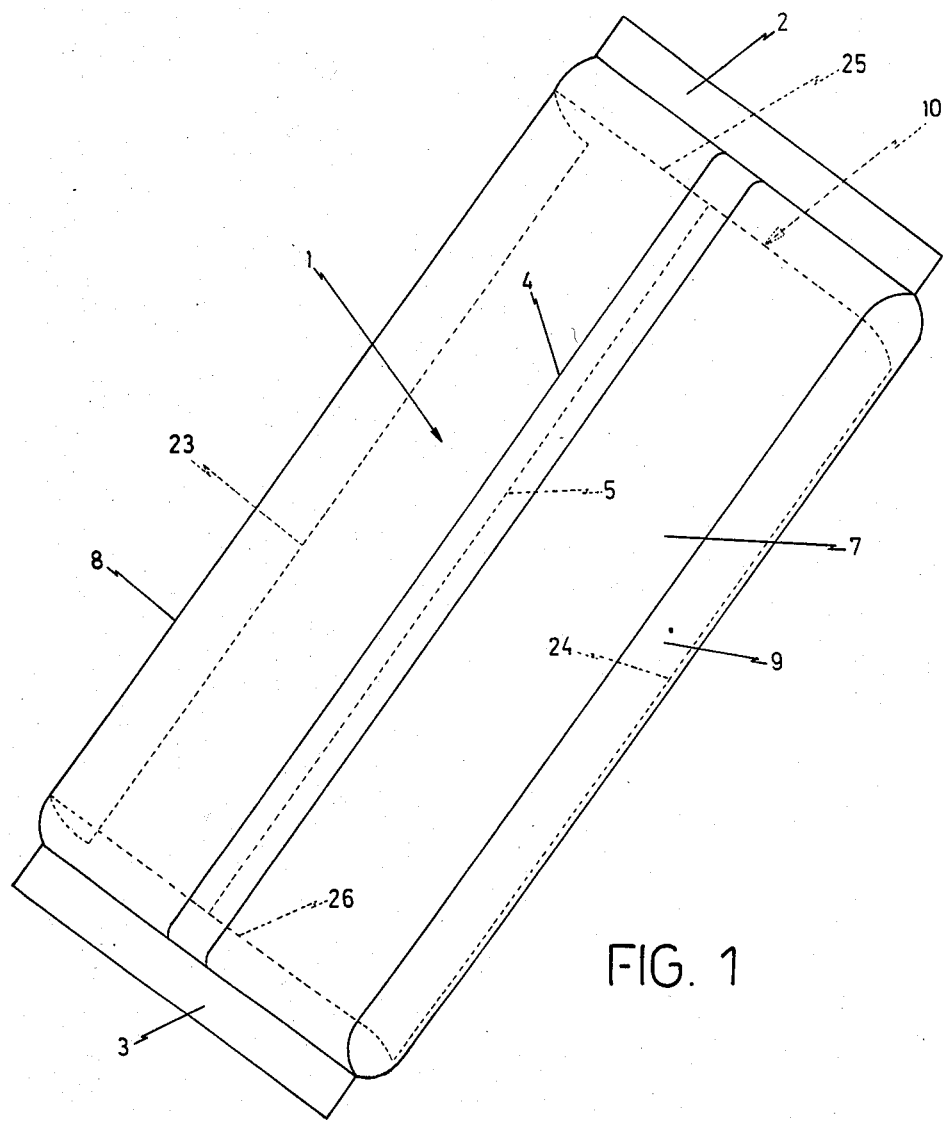
FIG. 1 is a perspective view of a sanitary napkin built in accordance with the present invention, wherein the garment-side of the sanitary napkin may be seen.

Having now more particular reference to FIGS. 1 to 4 of the drawings, there is shown a sanitary napkin designated by means of general reference character 1, which as is well known in the art generally comprises a pair of extreme tabs 2 and 3 for permitting grasping of the napkin 1, a fluid absorbent body-side face 6 and an impervious garment-side face 7, spaced by means of a pair of longitudinal side edges 8 and 9, which together with spaces 6 and 7 form a receptacle to contain all the various standard elements of the sanitary napkin which will be described in more deail hereinbelow, together with an integral bag 10 which will also be described in more detail hereinbelow. The garment-side face of the sanitary napkin in accordance with the present invention and designated by means of reference character 7, has a longitudinal slit 5 which runs through the axial center of the sanitary napkin as shown, and a pair of adhesive bands 11 and 12 placed on the face 7 adjacent the slit 5 as clearly shown in FIGS. 3 and 4 of the drawings. A protective band 13 is placed over the slit 5 and the adhesive bands 11 and 12, in order to fully cover said slit and to also protect said adhesive bands 11 and 12, as well as to preserve the same for use in attaching the sanitary napkin to an undergarment of the wearer as is well known in the art.

Figure 4:
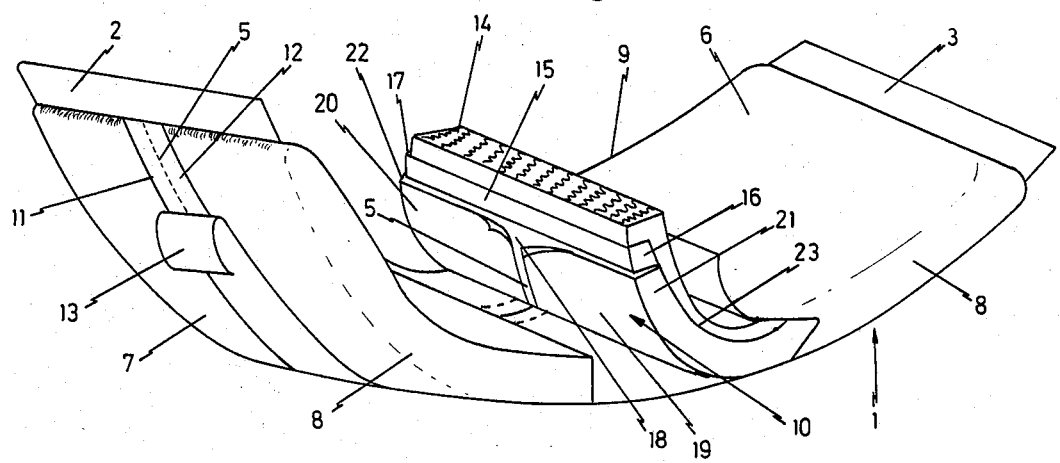
FIG. 4 is a perspective view of a sanitary napkin built in accordance with the present invention, with parts thereof broken away in order to show the inner structure of the napkin and of the disposal means integrally provided therein.

FIG. 4 shows the structure of the sanitary napkin built in accordance with the present invention in more detail, and it may be seen that the receptacle formed by faces 6 and 7 and side edges 8 and 9 and closed at its ends by means of tabs 2 and 3, is formed by means of a fluid pervious material to permit transmission of the body fluids into the receptacle, and within said receptacle an absorbent pad 14 is located, the body-side face of which receives the fluid transmitted by the face 6 of the receptacle of the napkin, to be absorbed thereby.

In order to avoid filtration of body fluid absorbed by the absorbing pad 14 towards the garment-side face of the sanitary napkin in accordance with the present invention and as is also well known in the art, it is preferred to place, on the garment-side face of the absorbing pad 14, a lamina 15 of an impervious material, which is bent along its side edges in order to form a pair of flanges 16 and 17 to cover at least partially the side edges of the absorbent pad 14, as well as the full garment-side face of said absorbent pad 14, whereby any filtration of body fluids outwardly of the absorbent pad 14 towards the garment-side face of the sanitary napkin is avoided, since all the fluids are kept in the absorbent pad 14 by the action of the impervious lamina 15 and the side flanges of said impervious lamina 16 and 17 described above.

In accordance with the present invention, a sheet 18 of an impervious material is placed on the back of said impervious lamina 15, with the side edges of said sheet folded over its edges 22 and 23 as shown in FIG. 4 of the drawings, in order to form a pair of flaps 19 and 20 which, together with the layer 18 of the impervious sheet, form a bag 10 which is fully integrated within the receptacle of the sanitary napkin 1, and which is capable of being opened by means of the slit 5 left between the side flaps 19 and 20, as will be described hereinbelow in more detail.

The disposal bag built in accordance with the present invention, therefore, merely comprises a double layer of an impervious material, particulary consisting of a layer 18 contiguous to the impervious lamina 15 described above, a pair of side edges 21 and 22 which cover the side flanges 16 and 17 of said impervious lamina, walls at 21 and 22, and a pair of flaps 19 and 20, opened at the center of the sanitary napkin, to form a longitudinal slit 5, which coincides with the slit 5 of the fluid pervious wrapping of the sanitary napkin, and is adhered thereto, in order to provide an integral device which in shape has no difference whatsoever to a sanitary napkin not containing said disposal bag 10.

The adhesive bands 11 and 12 are provided as described above along the sides of slit 5 on the garment-side face 7 of the wrapping of the napkin 1, and the protecting web 13 is placed over said adhesive bands 11 and 12 to fully cover the same as well as the slit 5 to maintain the same closed.

The sanitary napkin built in accordance with the invention and as described above in connection with FIGS. 1 to 4 of the drawings is sold to be used as shown in FIG. 1 of the drawings, with the bag 10 closed by the slit 5 which is in turn fully covered by the protecting band 4 which also covers the two adhesive bands 11 and 12 provided at both sides of slit 5. When the device is to be used by a wearer, the band 13 is completely removed thereby exposing, as is usual in the art, the adhesive bands 11 and 12 which in the particular non-used condition of the sanitary napkin is completely closed as shown in FIG. 1 of the drawings, whereby the adhesive bands 11 and 12 resemble one single band which is then used by the wearer to attach the sanitary napkin to an undergarment to be used.

Figure 5:
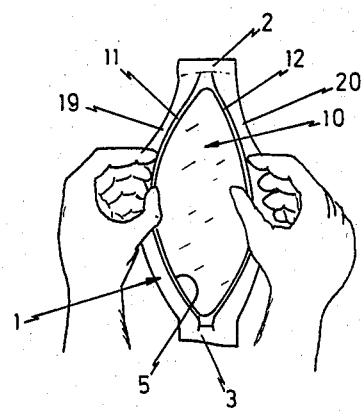
FIGS. 5, 6, 7 and 8 are sequential views showing the various steps to use the disposal means of the sanitary napkin in accordance with the present invention.
Figure 6:
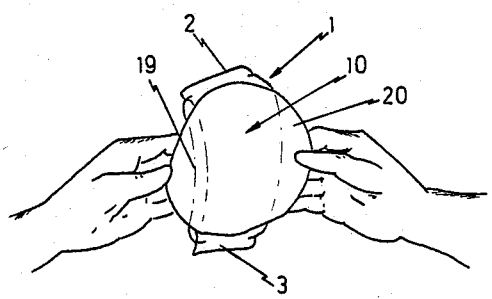
Figure 7:
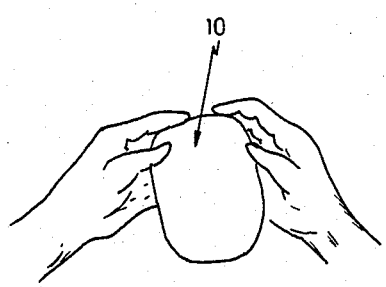
Figure 8:
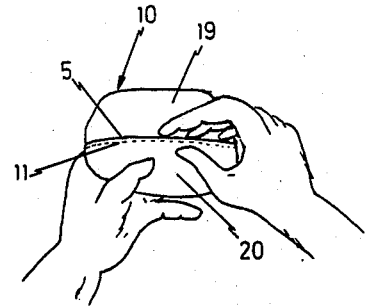

Once the sanitary napkin is used and the face 6 thereof is stained, the slit 5 is taken with both thumbs as shown in FIG. 5 of the drawings and opened in the form of an oval, to expose the interior of bag 10. The operation of inserting the used and stained sanitary napkin 1 into the bag 10 is continued to accomplish the turning of said bag 10 inside-out as shown in the sequence of FIGS. 6, 7 and 8. In FIG. 6, the bag 10 is shown in a partially inside-out turned position, with the flaps 19 and 20 located on the sides of the body of the sanitary napkin 1, and with the sanitary napkin partially bent in order to reduce the size thereof to enable the insertion of the full sanitary napkin 1 into the bag 10. In FIG. 7, the flaps 19 and 20 are placed on the back of the bag 10 as shown in said FIG. 7, with the slit 5 closed and the back turned inside-out, whereafter the adhesive bands 11 and 12 are used to adhere, for instance, flap 19 to the face 6 of the sanitary napkin, and to adhere flap 20 unto flap 19 in a slightly overlapped position, whereby the device is completely housed within bag 10 which is sealed hermetically, thereby producing a wrapped stained sanitary napkin which is fully contained and sealed within bag 10 turned inside-out, for the purpose of disposing of the same in a neat manner, and without the production of bad odors and strike-back of the body fluids or the like.

As the bag 10 is fully contained in a strictly flat position within the receptacle of the sanitary napkin which also contains the absorbing pad 14 and the impervious lamina 15, the bag 10 is absolutely incospicuous and as mentioned above, the shape of the sanitary napkin is no different to the shape of standard sanitary napkins not containing said bag, whereby there is no discomfort caused to the wearers of the article, and adhesive bands 11, 12 may be arranged much in the same manner as in a standard sanitary napkin not containing the bag 10. Mass production techniques may be easily used to produce this composite sanitary napkin with the bag 10 integrated inwardly of the same, thereby avoiding the existence of a self-contained bag on the bottom of the napkin and interference with the adhesive attachment of the napkin to the undergarment.

The bag 10 is fully integrated within the napkin and therefore the provision thereof is equivalent to the provision of one additional layer within the napkin, whereby this addition is quite suitable for using mass production techniques without any considerable increase in the costs.

The provision of the impervious material bag 10 in the form of a double layer within the body of the sanitary napkin, on the other hand, may permit the omission of the impervious lamina 15 which is normally inserted in sanitary napkins, whereby the costs are considerably reduced and the total cost of a napkin built in accordance with this slightly modified embodiment of the invention, may be regarded as being practically the same as the cost of production of a sanitary napkin not containing the bag 10 but containing the impervious lamina 15 which is indispensible for preventing filtration of the body fluids outwardly of the sanitary napkin. It will be obvious to any one skilled in the art that the provision of both the lamina 15 and the bag 10 of impervious materials, will offer a more secure preservation of the body fluids within the absorbent pad 14, but the alternative described in this paragraph is perfectly possible to keep the costs at a minimum, since the bag 10 is substituted for the impervious lamina 15 with exactly the same effects plus the effect of provising a receptacle which, when turned inside-out, will serve as a continent to hermetically enclose the used sanitary napkin without any staining, strike-back or bad odors produced.

Although in the above certain specific embodiments of the present invention have been shown and described, it is to be understood that many modifications thereof are possible. The present invention, therefore, is not to be restricted except insofar as is necessitated by the prior art and by the spirit of the appended claims.

What is claimed is:

1. A sanitary napkin comprising a fluid transmitting wrapper, a fluid absorbent pad housed within said wrapper, at least one adhesive band extending along the length of the outer surface of the garment-side face of said wrapping for attaching said napkin to an undergarment, a protecting web covering said adhesive band, and an integral disposal bag which comprises a pair of layers of an impervious material arranged between the back of said fluid absorbent pad and the garment-side of the wrapping, said layers also spanning the side edges of said absorbent pad and being formed by a single sheet of said impervious material folded over itself at its side edges and closed at its ends to constitute said bag, the garment-side layer of said bag being slit throughout its length by means of a cut at the mid line of said napkin for forming a pair of openable flaps, the margins of both of said flaps being provided with an outer adhesive band covered by said protecting web, said adhesive bands providing in use garment attaching means as well as bag sealing means when disposing of said napkin upon opening said flaps and turning said bag inside-out to completely wrap the used napkin.

2. A sanitary napkin according to claim 1 wherein a fluid impervious lamina is additionally located between the back surface of the absorbent pad and the front surface of said impervious bag, said impervious lamina also spanning the edges of said absorbent pad to assist in avoiding permeation of the body fluids towards the garment-side face of the napkin.

3. A sanitary napkin according to claim 1 wherein said fluid transmitting wrapper is sealed at its ends and projects outwardly thereof for forming a pair of flaps at each end of said napkin, said folded over single sheet of impervious material of the bag extending between the layers of said flaps to be sealed together therewith to thereby seal the ends of said impervious material layers to constitute said disposal bag.

4. A sanitary napkin according to claim 1 wherein said fluid transmitting wrapper is formed to provide a pair of elongated flaps, one at each end of said sanitary napkin, and said wrapping is sealed at the edges of said elongated flaps together with the ends of said layers of impervious material forming the disposal bag, whereby to provide an elongated disposal bag which may house the full length of the sanitary napkin including the elongated flaps.

* * * * *